US007048927B2

(12) United States Patent
Brooks et al.

(10) Patent No.: US 7,048,927 B2
(45) Date of Patent: *May 23, 2006

(54) BOTULINUM NEUROTOXIN ELUTING STENT

(75) Inventors: Gregory F. Brooks, Irvine, CA (US); Stephen Donovan, Capistrano Beach, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/628,905

(22) Filed: Jul. 28, 2003

(65) Prior Publication Data

US 2004/0142005 A1    Jul. 22, 2004

Related U.S. Application Data

(63) Continuation of application No. 10/114,740, filed on Apr. 1, 2002, now Pat. No. 6,767,544, which is a continuation of application No. 09/371,354, filed on Aug. 10, 1999, now Pat. No. 6,977,080.

(51) Int. Cl.
*A61K 39/00* (2006.01)
*A61K 39/08* (2006.01)

(52) U.S. Cl. .................. 424/184.1; 424/247.1
(58) Field of Classification Search ............... 604/508; 424/184.1, 247.1, 97.1, 164.1; 530/340
See application file for complete search history.

(56) References Cited

U.S. PATENT DOCUMENTS

| | | | |
|---|---|---|---|
| 5,092,841 A | 3/1992 | Spears | |
| 5,385,935 A | 1/1995 | Tamai et al. | |
| 5,437,291 A * | 8/1995 | Pasricha et al. | 128/898 |
| 5,562,907 A * | 10/1996 | Arnon | 424/236.1 |
| 5,766,605 A | 6/1998 | Sanders et al. | |
| 5,851,786 A * | 12/1998 | Johnson | 435/29 |
| 5,865,794 A | 2/1999 | Castro | 604/53 |
| 5,939,070 A * | 8/1999 | Johnson et al. | 424/194.1 |
| 5,989,280 A | 11/1999 | Euteneuer et al. | |
| 6,063,768 A * | 5/2000 | First | 514/14 |
| 6,102,904 A * | 8/2000 | Vigil et al. | 604/500 |
| 6,121,296 A * | 9/2000 | Schramm et al. | 514/343 |
| 6,183,506 B1 | 2/2001 | Penn et al. | |
| 6,190,404 B1 | 2/2001 | Palmaz et al. | |
| 6,196,230 B1 | 3/2001 | Hall et al. | |
| 6,217,608 B1 | 4/2001 | Penn et al. | |
| 6,238,872 B1 * | 5/2001 | Mosseri | 435/7.1 |
| 6,239,118 B1 | 5/2001 | Schatz et al. | |
| 6,241,758 B1 | 6/2001 | Cox | |
| 6,261,318 B1 | 7/2001 | Lee et al. | |
| 6,264,671 B1 | 7/2001 | Stack et al. | |
| 6,270,521 B1 | 8/2001 | Fischell et al. | |
| 6,290,961 B1 * | 9/2001 | Aoki et al. | 424/184.1 |
| 6,293,959 B1 | 9/2001 | Miller et al. | |
| 6,299,893 B1 * | 10/2001 | Schwartz et al. | 424/422 |
| 6,306,162 B1 | 10/2001 | Patel | |
| 6,306,423 B1 | 10/2001 | Donovan et al. | |
| 6,312,708 B1 | 11/2001 | Donovan | |
| 6,319,505 B1 * | 11/2001 | Aoki et al. | 424/236.1 |
| 6,344,055 B1 | 2/2002 | Shukov | |
| 6,383,509 B1 * | 5/2002 | Donovan et al. | 424/423 |
| 6,429,189 B1 * | 8/2002 | Borodic | 514/2 |
| 6,464,986 B1 | 10/2002 | Aoki et al. | |
| 6,579,847 B1 * | 6/2003 | Unger | 514/2 |
| 6,767,544 B1 * | 7/2004 | Brooks et al. | 424/247.1 |
| 2003/0185860 A1 * | 10/2003 | Brooks | 424/247.1 |

FOREIGN PATENT DOCUMENTS

| | | |
|---|---|---|
| WO | WO 00/04922 | 2/2000 |
| WO | 01/10458 * | 2/2001 |
| WO | WO 01/10458 A1 | 2/2001 |
| WO | WO 01/21213 A2 | 3/2001 |
| WO | 01/82947 * | 11/2001 |
| WO | WO 02/053181 A1 | 7/2002 |

OTHER PUBLICATIONS

Mukherjee et al, Expandable Metal Stents in Achalasia- Is There a Role?, Nov. 9, 2000, Elsevier Science Inc., vol. 95, 2185-2187.*

Rappuoli et al., Guidebook to Protein Toxins and Their Use in Cell Biology, 1997, Oxford University Press, pp. 66 and 108.*

Muniyappa, R. et al., Am. J. Physiol. Heart Cir. Physiol., vol. 278, (6) pp. H1762-H1768, Jun. 2000.*

Johnson, Eric. Clostridial toxins as therepeutic agents: benefits of nature's most toxic proteins. Annu Rev Microbiol 53: 551-575, 1999.*

Schmitt et al. Bacterial toxins: friends or foes? Emerg Infect Dis 5(2): 224-234, 1999.*

Muniyappa, R et al, Am. J. Physiol. Heart Cir. Physiol., vol. 278, (6) pp. H1762-H1768, Jun. 2000.*

DePalma, GD et al, Endoscopy, Dec. 2001, vol. 33(12), pp. 1027-1030.*

Maria, G et al, Diseases of the colon & Rectum, 2000, vol. 43(5), May, pp. 721-723.*

Tan, EK et al, Movement disorders, vol. 14(2), pp. 345-349, 1999.*

Tsuboi et al. Botulinum neurotoxin A blocks cholinergic ganglionic neurotransmission in the dog heart. Jpn J Pharmacol 89(3): 249-254, 2002.*

(Continued)

*Primary Examiner*—Lynette R. F. Smith
*Assistant Examiner*—Lakia J. Tongue
(74) *Attorney, Agent, or Firm*—Stephen Donovan; Martin A. Voet; Robert J. Baran

(57) ABSTRACT

The present invention provides for methods of treating cardiovascular diseases in a mammal. The methods include a step of administering an effective amount of a botulinum toxin directly to a blood vessel of a mammal thereby treating a cardiovascular disease.

5 Claims, No Drawings

OTHER PUBLICATIONS

Tsuboi et al. Inotropic, chronotropic, and dromotropic effects mediated via parasympathetic ganglia in the dog heart. Am J Physiol Heart Circ Physiol 279: H1201-H1207, 2000.*

Mangrum et al. The evaluation and management of bradycardia. N Eng J Med 342(10): 703-709, 2000.*

Aktories, K., et al., *Clostridium botulinum C3 ADP-Ribosyltransferase*, Current Topics in Microbiology and Immunology, vol. 175, 1992, 115-131.

Fauci, A.S., et al., *14th Edition Harrison's Principles of Internal Medicine*, McGraw-Hill pp 904-907, 1998.

Fiorentini, C. et al., *Bacterial toxins and the Rho GTP-binding protein: what microbes teach us about cell regulation*, Cell Death and Differentiation (1998) 5, pp. 720-728.

Nishiki, T., et al., *Morphological effects of clostridium botulinum C3 exoenzyme on cultured cells*, Jpn. J. Med. Sci. Biol. 43, 1990, 261-262.

U.S. Appl. No. 09/678,189, filed Oct. 4, 2000, Brooks et al.
U.S. Appl. No. 09/620,840, filed Jul. 21, 2000, Steward et al.
U.S. Appl. No. 09/489,667, filed Jan. 19, 2000, Donovan.
U.S. Appl. No. 09/922,093, filed Aug. 3, 2001, Donovan.
U.S. Appl. No. 09/625,098, filed Jul. 25, 2000, Donovan.
U.S. Appl. No. 09/910,346, filed Jul. 20, 2001, Steward.

Claus, D., et al., Botulinum Toxin: influence on respiratory heart rate variation, Mov Disord 1995 Sep.; 10(5): 574-579.

Girlanda, P., et al., Botulinum toxin therapy: distant effects on neuromuscular transmission and autonomic nervous system, J. Neurol Neurosurg Psychiatry 1992;55(9):844-5.

Lamanna, C., et al., Cardiac Effects of Botulinal Toxin, Arch Int Pharmacodyn Ther 1988; 293: 69-83.

Malnick, S., et al., Fatal heart block following treatment with botulinum toxin for achalasia, Am J Gastroenterol 2000;Nov.; 95(11):3333-3334.

Nebe, A., et al., No effects on heart-rate variability and cardiovascular reflex tests after boulinum toxin treatment of cervical dystonia, Mov Disord May, 1996; 11(3):337-339.

Sathyamoorthy, V., et al., Separation, purification, particial characterization and comparison of the heavy and light chains of botulinum neurotoxin types A, B and E, The J. of Biol. Chem, vol. 260, No. 19, Sep. 5, pp. 10461-10466, 1985.

Shone, C., et al., A 50-kDa fragment from the NH2-terminus of the heavy subunit of clostridium botulinum type A neurotoxin forms channels in lipid vesicles, Eur. J, Biochem 167, 175-180, 1987.

Author Unknown, Internet, Drug-coated stents help eliminate angioplasty problems, Mar. 18, 2002, www.cnn.com/2002/helath/03/18/heart.angioplasty.ap/index.html. 3 pgs.

Ayers, G.M., et al.; *Amiodarone Instilled Into the Canine Pericardial Sac Migrates Transmurally to Produce Electrophysiologic Effects and Suppress Atrial Fibrillation;* Journal of Cardiovascular Electrophysiology; vol. 7, No. 8; Aug. 1996; 713-721.

Lamanna, C., et al.; *Cardiac Effects of Botulinal Toxin; Arc. Int. Pharmacodyn.*; 1988; vol. 293; 69-83.

Lamanna, C.; *Thoughts on Action of Botulinum Toxin Suggested by Reversibility of Heart Effects; Botulinum and Tetanus Neurotoxins* (edited by Dasgupta, B.R.); 1993 Plenum Press; 333-335.

McDermott, D.A., et al.; *Use of an Indwelling Catheter for Examining Cardiovascular Responses to Pericardial Administration of Bradykinin in Rat; Cardiovascular Research*; 1995; vol. 30; 39-46.

Galardi et al.: "The Local Injection of Botulinum Toxin Can Effect the Neural Control of Heart Rate Variability.", Nerology, vol. 44, 1994, pp. A307-A308.

Kimura et al.; "Negative Chronotropic Effect of Botulinum Toxin on Neonatal Rat Cardiac Mycocytes." Biochem. Biophys. Res. Comm., vol. 244, 1998, pp. 275-279.

Dickson, E., *Studies on the Manner in which the Toxin of Clostridium Botulinum Acts Upon the Body*, J. Exper Med 37: 711-31 (1923) d.

Fauci, A., *Harrison's Principles of Internal Medicine* fourteenth edition (1997), McGraw Hill.

Nattel, S., *Comparative Mechanisms of Action of Antiarrhythmic Drugs*, Am J. Cardiol, 72: 13F-17F (1993).

Wit, A., *Electrophysiological Basis for Antiarrhythmic Drug Action*, Clin. Physiol. Biochem. 3: 127-134 (1985).

Waxman, S., *Persistent Primary Coronary Dilation Induced by Transatrial Delivery of Nitroglycerin into the Pericardial Space: A Novel Approach for Local Cardiac Drug Delivery*, J Am Coll Cardiol 33: (7); 2073-2077 (1999).

Claus, D., *Botulinum Toxin: Influence on Respiratory Heart rate Variation*, Mov Disord 10(5): 574-9 (1995).

Kimura, K., *Negative Chronotropic Effect of Botulinum Toxin on Neonatal Rat Cardiac Myocytes*, Biochem Biophys Res Commun 6; 244 91):275-9 (1998).

Nebe, A., *No Effects on Heart-Rate Variability and Cardiovascular Reflex Tests After Botulinum Toxin Treatment of Cervical Dystonia*, Mov Disord; 11 (3): 337-9 (1996).

Glaradi, G., *The Local Injection of Botulinum Toxin can Affect the Neural Control of Heart Rate Variability*, Neural 44; (Sup 2): A307-A308 (1994).

Laham, R., *Therapeutic Myocardial Angiogenesis Using Percutaneous Intrapericardial Drug Delivery*, Clin Cardiol; 22 (supp 1): 16-19 (1999).

Laham, R., *Subxyphoid Access of the Normal pericardium: A Novel Drug Delivery Technique, Cath & Cardiovasc Inter* 47: 109-111 (1999).

Sonobe, T., *Development of Intracoronary Local Adhesive delivery Technique*, Int. J Artic Organs 20(6); 310-326 (1997).

Avitall, B., *Iontophoretic Transmyocardial Drug Delivery. A Novel Approach to Antiarrhythmic Drug Therapy*, Circulation 85: 1582-93 (1992).

Labhasetwar V., *Epicardial Administration of Ibutilide from Polyurethane Matrices: Effects on Defibrillation Threshold and Electrophysiologic Parameters* J Cardiovasc Pharmacol 24: 826-40 (1994).

Lambert, C., *Local Drug Delivery*, Cath & Cardiovasc Diagn 41: 231 (1997).

Glazier, J., *Site-Specific Intracoronary Thombolysis With Urokinase-Coated Hydrogel Balloons: Acute and Follow-Up Studies in 95 Patients*, Cath & Cardiovase Diagn 41: 246-253 (1997).

Bartorelli, A., *Local Heparin Delivery Prior to Coronary Stent Implantation: Acute and Six Month Clinical And Angiographic Results*, Cath & Cardiovasc Diagn 42: 313-320 (1997).

Nebe, A., *Influence of Botulinum Toxin Type A on the Heart Rate Variability in Patients with Cervical Dystonia*, Mov Dis 10; 3: 389 (1995).

Claus, D., *Distant Effects of Botulinum Toxin on Autonomic Cardiac Reflexes*, Mov Dis 10: 3: 389 (1995).

Thomas, C., *Local Intracoronary Heparin Delivery With a Microporous Balloon Catheter*, Amer Heart J 132; 5: 969-972 (1996).

Camemzind, E., *Site-Specific Intravascular Administration of drugs: History of a Method Applicable in Humans*, Cath & Cardiovasc Diagn 41: 342-347 (1997).

* cited by examiner

BOTULINUM NEUROTOXIN ELUTING STENT

BACKGROUND

This is a continuation of application Ser. No. 10/114,740, filed Apr. 1, 2002, issued as U.S. Pat. No. 6,767,544, which is a continuation in part of application Ser. No, 09/371,354, filed Aug. 10, 1999, issued as U.S. Pat. No. 6,977,080. The entire contents of these prior patent applications are incorporated herein by reference.

BACKGROUND

The present invention relates to methods of preventing or reducing restenosis that may occur in blood vessels after mechanically expanding the diameter of an occluded blood vessel.

Atherosclerosis is a progressive disease wherein fatty, fibrous, calcific, or thrombotic deposits produce atheromatous plaques, within and beneath the intima which is the innermost layer of arteries. Atherosclerosis tends to involve large and medium sized arteries. The most commonly affected are the aorta, iliac, femoral, coronary, and cerebral arteries. Clinical symptoms occur because the mass of the atherosclerotic plaque reduces blood flow through the afflicted artery, thereby compromising tissue or organ function distal to it.

Percutaneous transluminal coronary angioplasty is a non-surgical method for treatment of coronary atherosclerosis. In this procedure, an inflatable balloon is inserted in a coronary artery in the region of arterial narrowing. Inflation of the balloon for 15–30 seconds results in an expansion of the narrowed lumen or passageway. Because residual narrowing is usually present after the first balloon inflation, multiple or prolonged inflations are routinely performed to reduce the severity of the residual tube narrowing.

Stents are often used in combination with coronary balloon angioplasty. Typically, a stent is used to brace the blood vessel open after an initial expansion of the narrowed blood vessel by a balloon. Self expanding stents are also used to expand and hold open occluded blood vessels. Various stents and their use are disclosed in U.S. Pat. Nos. 6,190,404; 6,344,055; 6,306,162; 6,293,959; 6,270,521; 6,264,671; 6,261,318; 6,241,758; 6,217,608; 6,196,230; 6,183,506; 5,989,280. The disclosure of each of these patents is incorporated in its entirety herein by reference.

One problem with angioplasty is that following the procedure restenosis, or recurrence of the obstruction, may occur. Tears in the wall expose blood to foreign material and proteins, such as collagen, which are highly thrombogenic. Resulting clots can contain growth hormones which may be released by platelets within the clot. Additionally, thrombosis may cause release of growth hormones and cytokines by cells from macrophages. Growth hormones may cause smooth muscle cells and fibroblasts to aggregate in the region and multiply. Further, following angioplasty there is often a loss of the single layer of cells that normally covers the internal surface of blood vessels which leads to thrombosis. The combination of tearing of the blood vessel wall and the loss of the endothelial layer often generates an internal blood vessel surface which is quite thrombogenic. Restenosis may result from the proliferation of smooth muscle cells, which normally reside within the arterial wall, in the area of the injury in response to the thrombosis.

Angioplasty procedures also produce injuries in the arterial wall which become associated with inflammation. Any kind of inflammatory response may cause growth of new tissue, for example, scar tissue, which may contribute to restenosis.

One of the other major causes of restenosis following angioplasty may be that the injured arterial wall may exhibit a reduced hemocompatability compared to that associated with a normal arterial wall. Adverse responses which are associated with reduced hemocompatability include platelet adhesion, aggregation, and activation; thrombosis; inflammatory cell reactions such as adhesion and activation of monocytes or macrophages; and the infiltration of leukocytes into the arterial wall.

Restenosis is a serious problem that may occur in over one third of all coronary angioplasty patients. Therefore, there exists a need for methods to reduce or eliminate the occurrence of restenosis which may follow procedures to mechanically expand an occluded blood vessel.

Botulinum Toxin

The anaerobic, Gram positive bacterium *Clostridium botulinum* produces a potent polypeptide neurotoxin botulinum toxin, which causes a neuroparalytic illness in humans and animals referred to as botulism. The spores of *Clostridium botulinum* are found in soil and can grow in improperly sterilized and sealed food containers of home based canneries, which are the cause of many of the cases of botulism. The effects of botulism typically appear 18 to 36 hours after eating the foodstuffs infected with a *Clostridium botulinum* culture or spores. The botulinum toxin can apparently pass unattenuated through the lining of the gut and attack peripheral motor neurons. Symptoms of botulinum toxin intoxication can progress from difficulty walking, swallowing, and speaking to paralysis of the respiratory muscles and death.

Botulinum toxin type A ("BoNT/A") is the most lethal natural biological agent known to man. About 50 picograms of botulinum toxin (purified neurotoxin complex) serotype A is a $LD_{50}$ in mice. One unit (U) of botulinum toxin is defined as the $LD_{50}$ upon intraperitoneal injection into female Swiss Webster mice weighing 18–20 grams each. Seven immunologically distinct botulinum, neurotoxins have been characterized, these being respectively botulinum neurotoxin serotypes A, B, $C_1$, D, E, F and G each of which is distinguished by neutralization with serotype-specific antibodies. The different serotypes of botulinum toxin vary in the animal species that they affect and in the severity and duration of the paralysis they evoke. For example, it has been determined that BoNt/A is 500 times more potent, as measured by the rate of paralysis produced in the rat, than is botulinum toxin serotype B (BoNT/B). Additionally, botulinum toxin type B ("BoNt/B") has been determined to be non-toxic in primates at a dose of 480 U/kg which is about 12 times the primate $LD_{50}$ for BoNt/A. Botulinum toxin apparently binds with high affinity, to cholinergic motor neurons, is translocated into the neuron and blocks the release of acetylcholine.

Botulinum toxins have been used in clinical settings for the treatment of neuromuscular disorders characterized by hyperactive skeletal muscles. BoNt/A has-been approved by the U.S. Food and Drug Administration for the treatment of blepharospasm, strabismus, hemifacial spasm and cervical dystonia. Additionally, a botulinum toxin type B has been approved by the FDA for the treatment of cervical dystonia. Non-serotype A botulinum toxin serotypes apparently have a lower potency and/or a shorter duration of activity as compared to BoNt/A. Clinical effects of peripheral intramuscular BoNt/A are usually seen within one week of injection. The typical duration of symptomatic relief from a single intramuscular injection of BoNt/A averages about three months.

Although all the botulinum toxins serotypes apparently inhibit release of the neurotransmitter acetylcholine at the neuromuscular junction, they do so by affecting different neurosecretory proteins and/or cleaving these proteins at different sites. For example, botulinum serotypes A and E both cleave the 25 kiloDalton (kD) synaptosomal associated protein (SNAP-25), but they target different amino acid sequences within this protein. BoNT/B, D, F and G act on vesicle-associated protein (VAMP, also called synaptobrevin), with each serotype cleaving the protein at a different site. Finally, botulinum toxin serotype $C_1$ (BoNT/$C_1$) has been shown to cleave both syntaxin and SNAP-25. These differences in mechanism of action may affect the relative potency and/or duration of action of the various botulinum toxin serotypes.

Regardless of serotype, the molecular mechanism of toxin intoxication appears to be similar and to involve at least three steps or stages. In the first step of the process, the toxin binds to the presynaptic membrane of the target neuron through a specific interaction between the H chain and a cell surface receptor; the receptor is thought to be different for each serotype of botulinum toxin and for tetanus toxin. The carboxyl end segment of the H chain, $H_C$, appears to be important for targeting of the toxin to the cell surface.

In the second step, the toxin crosses the plasma membrane of the poisoned cell. The toxin is first engulfed by the cell through receptor-mediated endocytosis, and an endosome containing the toxin is formed. The toxin then escapes the endosome into the cytoplasm of the cell. This last step is thought to be mediated by the amino end segment of the H chain, $H_N$, which triggers a conformational change of the toxin in response to a pH of about 5.5 or lower. Endosomes are known to possess a proton pump which decreases intra endosomal pH. The conformational shift exposes hydrophobic residues in the toxin, which permits the toxin to embed itself in the endosomal membrane. The toxin then translocates through the endosomal membrane into the cytosol.

The last step of the mechanism of botulinum toxin activity appears to involve reduction of the disulfide bond joining the H and L chain. The entire toxic activity of botulinum and tetanus toxins is contained in the L chain of the holotoxin; the L chain is a zinc (Zn++) endopeptidase which selectively cleaves proteins essential for recognition and docking of neurotransmitter-containing vesicles with the cytoplasmic surface of the plasma membrane, and fusion of the vesicles With the plasma membrane. Tetanus neurotoxin, botulinum toxin/B/D,/F, and/G cause degradation of synaptobrevin (also called vesicle-associated membrane protein (VAMP)), a synaptosomal membrane protein. Most of the VAMP present at the cytosolic surface of the synaptic vesicle is removed as a result of any one of these cleavage events. Each toxin specifically cleaves a different bond.

The molecular weight of the botulinum toxin protein molecule, for all seven of the known botulinum toxin serotypes, is about 150 kD. Interestingly, the botulinum toxins are released by Clostridial bacterium as complexes comprising the 150 kD botulinum toxin protein molecule along with associated non-toxin proteins. Thus, the BoNt/A complex can be produced by Clostridial bacterium as 900 kD, 500 kD and 300 kD forms. BoNT/B and $C_1$ are apparently produced as only a 500 kD complex. BoNt/D is produced as both 300 kD and 500 kD complexes. Finally, BoNT/E and F are produced as only approximately 300 kD complexes. The complexes (i.e. molecular weight greater than about 150 kD) are believed to contain a non-toxin hemaglutinin protein and a non-toxin and non-toxic nonhemaglutinin protein. These two non-toxin proteins (which along with the botulinum toxin molecule comprise the relevant neurotoxin complex) may act to provide stability against denaturation to the botulinum toxin molecule and protection against digestive acids when toxin is ingested. Additionally, it is possible that the larger (greater than about 150 kD molecular weight) botulinum toxin complexes may result in a slower rate of diffusion of the botulinum toxin away from a site of intramuscular injection of a botulinum toxin complex.

In vitro studies have indicated that botulinum toxin inhibits potassium cation induced release of both acetylcholine and norepinephrine from primary cell cultures of brainstem tissue. Additionally, it has been reported that botulinum toxin inhibits the evoked release of both glycine and glutamate in primary cultures of spinal cord neurons and that in brain synaptosome preparations botulinum toxin inhibits the release of each of the neurotransmitters acetylcholine, dopamine, norepinephrine, CGRP and glutamate.

BoNt/A can be obtained by establishing and growing cultures of *Clostridium botulinum* in a fermenter and then harvesting and purifying the fermented mixture in accordance with known procedures. All the botulinum toxin serotypes are initially synthesized as inactive single chain proteins which must be cleaved or nicked by proteases to become neuroactive. The bacterial strains that make botulinum toxin serotypes A and G possess endogenous proteases and serotypes A and G can therefore be recovered from bacterial cultures in predominantly their active form. In contrast, botulinum toxin serotypes $C_1$, D and E are synthesized by nonproteolytic strains and are therefore typically unactivated when recovered from culture. Serotypes B and F are produced by both proteolytic and nonproteolytic strains and therefore can be recovered in either the active or inactive form. However, even the proteolytic strains that produce, for example, the BoNt/B serotype only cleave a portion of the toxin produced. The exact proportion of nicked to unnicked molecules depends on the length of incubation and the temperature of the culture. Therefore, a certain percentage of any preparation of, for example, the BoNt B toxin is likely to be inactive, possibly accounting for the known significantly lower potency of BoNt/B as compared to BoNt/A. The presence of inactive botulinum toxin molecules in a clinical preparation will contribute to the overall protein load of the preparation, which has been linked to increased antigenicity, without contributing to its clinical efficacy. Additionally, it is known that BoNt/B has, upon intramuscular injection, a shorter duration of activity and is also less potent than BoNt/A at the same dose level.

It has been reported (as exemplary examples) that BoNt/A has been used clinically as follows:

(1) about 75–125 units of BOTOX®[1] per intramuscular injection (multiple muscles) to treat cervical dystonia;

[1]Available from Allergan, Inc., of Irvine, Calif. under the tradename BOTOX®.

(2) 5–10 units of BOTOX® per intramuscular injection to treat glabellar lines (brow furrows) (5 units injected intramuscularly into the procerus muscle and 10 units injected intramuscularly into each corrugator supercilii muscle);

(3) about 30–80 units of BOTOX® to treat constipation by intrasphincter injection of the puborectalis muscle;

(4) about 1–5 units per muscle of intramuscularly injected BOTOX® to treat blepharospasm by injecting the lateral pre-tarsal orbicularis oculi muscle of the upper lid and the lateral pre-tarsal orbicularis oculi of the lower lid.

(5) to treat strabismus, extraocular muscles have been injected intramuscularly with between about 1–5 units of BOTOX®, the amount injected varying based upon both the size of the muscle to be injected and the extent of muscle paralysis desired (i.e. amount of diopter correction desired).

(6) to treat upper limb spasticity following stroke by intramuscular injections of BOTOX® into five different upper limb flexor muscles, as follows:
(a) flexor digitorum profundus 7.5 U to 30 U
(b) flexor digitorum sublimus: 7.5 U to 30 U
(c) flexor carpi ulnaris: 1 U to 40 U
(d) flexor carpi radialis: 15 U to 60 U
(e) biceps brachii: 50 U to 200 U. Each of the five indicated muscles has been injected at the same treatment session, so that the patient receives from 90 U to 360 U of upper limb flexor muscle BOTOX® by intramuscular injection at each treatment session.

The tetanus neurotoxin acts mainly in the central nervous system, while botulinum neurotoxin acts at the neuromuscular junction; both act by inhibiting acetylcholine release from the axon of the affected neuron into the synapse, resulting in paralysis. The effect of intoxication on the affected neuron is long lasting and until recently has been thought to be irreversible. The tetanus neurotoxin is known to exist in one immunologically distinct serotype.

Acetylcholine

Typically only a single type of small molecule neurotransmitter is released by each type of neuron in the mammalian nervous system. The neurotransmitter acetylcholine is secreted by neurons in many areas of the brain, but specifically by the large pyramidal cells of the motor cortex, by several different neurons in the basal ganglia, by the motor neurons that innervate the skeletal muscles, by the preganglionic neurons of the autonomic nervous system (both sympathetic and parasympathetic), by the postganglionic neurons of the parasympathetic nervous system, and by some of the postganglionic neurons of the sympathetic nervous system. Essentially, only the postganglionic sympathetic nerve fibers to the sweat glands, the piloerector muscles and a few blood vessels are cholinergic and most of the postganglionic neurons of the sympathetic nervous system secret the neurotransmitter norepinephine. In most instances acetylcholine has an excitatory effect. However, acetylcholine is known to have inhibitory effects at some of the peripheral parasympathetic nerve endings, such as inhibition of the heart by the vagal nerve.

The efferent signals of the autonomic nervous system are transmitted to the body through either the sympathetic nervous system or the parasympathetic nervous system. The preganglionic neurons of the sympathetic nervous system extend from preganglionic sympathetic neuron cell bodies located in the intermediolateral horn of the spinal cord. The preganglionic sympathetic nerve fibers, extending from the cell body, synapse with postganglionic neurons located in either a paravertebral sympathetic ganglion or in a prevertebral ganglion. Since, the preganglionic neurons of both the sympathetic and parasympathetic nervous system are cholinergic, application of acetylcholine to the ganglia will excite both sympathetic and parasympathetic postganglionic neurons.

Acetylcholine activates two types of receptors, muscarinic and nicotinic receptors. The muscarinic receptors are found in all effector cells stimulated by the postganglionic neurons of the parasympathetic nervous system, as well as in those stimulated by the postganglionic cholinergic neurons of the sympathetic nervous system. The nicotinic receptors are found in the synapses between the preganglionic and postganglionic neurons of both the sympathetic and parasympathetic. The nicotinic receptors are also present in many membranes of skeletal muscle fibers at the neuromuscular junction.

Acetylcholine is released from cholinergic neurons when small, clear, intracellular vesicles fuse with the presynaptic neuronal cell membrane. A wide variety of non-neuronal secretory cells, such as, adrenal medulla (as well as the PC12 cell line) and pancreatic islet cells release catecholamines and insulin, respectively, from large dense-core vesicles. The PC12 cell line is a clone of rat pheochromocytoma cells extensively used as a tissue culture model for studies of sympathoadrenal development. Botulinum toxin inhibits the release of both types of compounds from both types of cells in vitro, permeabilized (as by electroporation) or by direct injection of the toxin into the denervated cell. Botulinum toxin is also known to block release of the neurotransmitter glutamate from cortical synaptosomes cell cultures.

SUMMARY

The present invention provides for methods to treat cardiovascular diseases in a mammal, for example, in a human. The methods include a step of administering an effective amount of a botulinum toxin directly to a blood vessel of a mammal to treat a cardiovascular disease. In one embodiment, treating the cardiovascular disease prevents restenosis.

In one embodiment of the invention, the mammal is having or has had a cardiovascular procedure. In one embodiment, the cardiovascular procedure is an arterial cardiovascular procedure, for example, a coronary arterial cardiovascular procedure.

In one embodiment, the cardiovascular procedure includes an angioplasty procedure. In one embodiment, the angioplasty includes the step of inserting a stent into the blood vessel of the mammal. In another embodiment, the angioplasty does not include the step of inserting a stent into a blood vessel. The angioplasty procedure may be, for example, balloon angioplasty. In one embodiment, the balloon angioplasty includes the use of a stent. For example, a stent may be inserted into the blood vessel during the balloon angioplasty.

The procedure is not limited to use of a balloon. Any device that may be used to mechanically open a constricted blood vessel, for example, a spring or other expanding device, may be used to perform an angioplasty.

The step of administering the botulinum toxin may include a step of injecting the botulinum toxin into a wall of the blood vessel. In particular, the toxin may be injected into the intima, media and/or adventia layers of the blood vessel. Further, the step of administering may be accomplished using a stent which has been coated or impregnated with botulinum toxin.

In one embodiment of the present invention, the botulinum toxin reduces or eliminates damage to a blood vessel. Examples of damage that may occur are stretching and/or tearing of a blood vessel or any other damage that may occur to the blood vessel as a result of mechanically expanding the inner diameter of the blood vessel. In one embodiment, the botulinum toxin reduces or eliminates damage to the blood vessel, at least in part, by dilating the blood vessel. In another embodiment, the botulinum toxin reduces or eliminates damage to the blood vessel, at least in part, by reducing or eliminating inflammation of the blood vessel.

In accordance with the present invention, the botulinum toxin may be any botulinum toxin including botulinum toxin types A, B, C, D, E, F, G or mixtures thereof or combinations thereof, including a modified, hybrid or chimeric botulinum toxin.

Further in accordance with the present invention, there are provided methods to prevent restenosis in a blood vessel in a mammal which may occur following a cardiovascular procedure. In one embodiment, the method includes a step of administering to the mammal an effective amount of botulinum toxin thereby preventing restenosis in a blood vessel.

Still further in accordance with the present invention there are provided methods to prevent restenosis in a mammal by preventing damage in a blood vessel which may occur during or following a cardiovascular procedure. In one embodiment, the method includes the step of administering to a mammal an effective amount of a botulinum toxin thereby preventing damage in the blood vessel and preventing restenosis.

The present invention also provides for methods to prevent restenosis in a mammal by preventing inflammation in a blood vessel which may occur during or following a cardiovascular procedure. In one embodiment, the method includes the step of administering to a mammal an effective amount of the botulinum toxin thereby preventing inflammation in the blood vessel and preventing restenosis.

Further, the present invention provides for methods to prevent restenosis in a mammal by dilating a blood vessel proceeding, during or following a cardiovascular procedure. In one embodiment, the method includes the step of administering to a mammal an effective amount of the botulinum toxin thereby dilating the blood vessel and preventing restenosis.

Still further, the present invention provides for compositions for use in cardiovascular procedures. In one embodiment, these compositions include a stent with a botulinum toxin attached to the stent or imbedded in the stent. The botulinum toxin may be any botulinum toxin including botulinum toxin type A, B, C, D, E, F, G or combinations thereof or mixtures thereof.

Any feature or combination of features described herein are included within the scope of the present invention provided that the features included in any such combination are not mutually inconsistent as will be apparent from the context, this specification, and the knowledge of one of ordinary skill in the art.

Additional advantages and aspects of the present invention are apparent in the following detailed description and claims.

DEFINITIONS

"Agent" is defined as a neurotoxin, for example, a botulinum toxin, for use in accordance with the present invention. An agent may be a fragment of a neurotoxin, a modified neurotoxin or a variant neurotoxin that possesses some or all of the biological activity of an unmodified neurotoxin.

"Angioplasty" means any procedure where the inner diameter of a blood vessel is mechanically expanded.

A "botulinum toxin" may refer to native botulinum toxin or a functional fragment of a botulinum toxin or a modified botulinum toxin. In addition, botulinum toxins with amino acid deletions, additions, alterations or substitutions that delete, add, alter or substitute a single amino acid, or a small percentage of amino acids (for example, less than about 5%, or for example, less than about 1%) are conservatively modified variations of botulinum toxins. Where one or more substitutions of an amino acid(s) with a chemically similar amino acid are made in a botulinum toxin, this also results in a conservatively modified variation of a botulinum toxin. Tables providing functionally similar amino acids are well known in the art. The following five groups each contain amino acids that are conservative substitutions for one another: Aliphatic: Glycine (G), Alanine (A), Valine (V), Leucine (L), Isoleucine (I); Aromatic: Phenylalanine (F), Tyrosine (Y), Tryptophan (W); Sulfur-containing: Methionine (M), Cysteine (C); Basic: Arginine (R), Lysine (K), Histidine (H); Acidic: Aspartic acid (D), Glutamic acid (E), Asparagine (N), Glutamine (Q). See also, Creighton (1984) Proteins, W.H. Freeman and Company. Conservatively modified variations of native botulinum toxins are included within the scope of the meaning of "botulinum toxin."

"Cardiovascular" means pertaining to blood vessels, for example, blood vessels of the heart.

"Clostridial toxin" or "Clostridial neurotoxin" means a toxin produced naturally by the genus of bacteria Clostridium. For example, Clostidial toxins include, but are not limited to, botulinum toxins, tetanus toxins, difficile toxins and butyricum toxins. A Clostridial toxin can also be made by known recombinant means by a non-Clostridial bacterium.

"Combination" means an ordered sequence of elements. For example, a combination of botulinum toxins may mean administration of botulinum toxin E, followed by administration of botulinum toxin type A, followed by administration of botulinum toxin type B. This is opposed to a "mixture" where, for example, different toxin types are combined prior to administration.

"Damage" means tearing, scratching, stretching, scraping, bruising and/or inflammation or injury caused by inflammation or other injury that may occur in a blood vessel undergoing a procedure, for example, a procedure where the inner diameter of the blood vessel is expanded using mechanical force.

"Fragment" means an amino acid sequence that comprises five amino acids or more of the native amino acid sequence up to a size of minus at least one amino acid from the native sequence. For example, a fragment of a botulinum toxin type A light chain comprises five or more amino acids of the amino acid sequence of the native botulinum toxin type A light chain up to a size of minus one amino acid from the native light chain.

"$H_C$" means a fragment obtained from the H chain of a Clostridial toxin which is equivalent, for example functionally equivalent, to the carboxyl end fragment of the H chain, or the portion corresponding to that fragment in the intact H chain involved in binding to a cell surface or cell surface receptor.

"$H_N$" means a fragment or variant obtained from an H chain of a Clostridial toxin which may be functionally equivalent to the portion of an intact H chain involved in the translocation of at least the L chain across an intracellular endosomal membrane into a cytoplasm of a cell. An $H_N$, may result from an $H_C$ being removed from an H chain. An $H_N$ may also result from an H chain being modified such that its $H_C$ no longer binds to cholinergic cell surfaces.

"Heavy chain" means the heavy chain of a Clostridial neurotoxin or a fragment or variant of an $H_N$ of a Clostridial neurotoxin. A heavy chain may have a molecular weight of about 100 kD and can be referred to as H chain, or as H.

"LH$_N$" means a fragment obtained from a Clostridial neurotoxin that contains the L chain coupled to an H$_N$. LH$_N$ can be obtained from the intact Clostridial neurotoxin by proteolysis, so as to remove or to modify the H$_C$ domain.

"Light chain" means the light chain of a Clostridial neurotoxin or a fragment or variant of a light chain of a Clostridial neurotoxin. A light chain may have a molecular weight of about 50 kD, and can be referred to as L chain, L, or as the proteolytic domain of a Clostridial neurotoxin.

"Linker" means a molecule which couples two or more other molecules or components together.

A "modified neurotoxin" means a neurotoxin that has a non-native component covalently attached to the neurotoxin and/or a native portion of the neurotoxin missing. For example, a modified botulinum toxin may be a light chain of a botulinum toxin with a substance P molecule covalently attached.

"Neurotoxin" or "toxin" means a substance that inhibits neuronal function or cellular secretion. Clostridial toxins are examples of a neurotoxin.

"Prevent" means to keep from occurring in whole or in part.

"Reduce" means to make smaller in magnitude (e.g. size, quantity or number). The reduction may be about 1% to about 100%. For example, the reduction may be between about 1% and about 10% or between about 10% and about 20% or between about 10% and about 30% or between about 10% and about 40% or between about 10% and about 50% or between about 10% and about 60% or between about 10% and about 70% or between about 10% and about 80% or between about 10% and about 90% or between about 10% and about 100%.

"Spacer" means a molecule or set of molecules which physically separate and/or add distance between components of agents for use in accordance with the invention.

"Substantially" means largely but not entirely. For example, substantially may mean about 10% to about 99.999%, about 20% to about 99.999%, about 30% to about 99.999%, about 40% to about 99.999% or about 50% to about 99.999%.

"Targeting component" means a molecule that has a specific binding affinity for a cell surface or cell surface receptor.

"Variant" means a molecule or peptide which is substantially the same as that of a disclosed molecule or peptide in its structure and function. For example, a variant of a specified light chain may have amino acid sequence differences when compared to the amino acid sequence of the specified light chain. Variants may be considered to be equivalent to the specifically disclosed molecules and as such are within the scope of the invention.

DESCRIPTION

The present invention is, in part, based upon the discovery that a neurotoxin, for example, botulinum toxin, is useful for treating cardiovascular disease, for example, treating cardiovascular disease in a patient who has undergone, or is undergoing, a cardiovascular procedure. In one embodiment, the present invention provides for methods to reduce or eliminate restenosis following a cardiovascular procedure.

One skilled in the art will appreciate that the herein disclosed methods may find application in any blood vessel in the body including, but not limited to, coronary (heart), cerebral (brain), Carotid (neck), Renal (kidney), Visceral (abdominal), Iliac (hip), Femoropopliteal (thigh), Infrapopliteal (knee) blood vessels.

The invention comprises application of a neurotoxin, for example, a botulinum toxin, to a blood vessel of a patient who is undergoing or will undergo or has undergone a procedure that may, directly or indirectly, lead to damage of a blood vessel, for example, a coronary artery. In one embodiment, the present invention provides for methods to treat a patient undergoing an angioplasty procedure such that restenosis is reduced or eliminated following the procedure. In one embodiment, the angioplasty includes use of a stent, for example, a self expanding stent. In another embodiment, the angioplasty is balloon angioplasty. In another embodiment, the angioplasty is balloon angioplasty that includes use of a stent. In another embodiment, the angioplasty is balloon angioplasty that does not include use of a stent.

Without wishing to limit the present invention to any theory or mechanism of operation, it is thought that the present methods prevent damage to a blood vessel which may occur in association with a mechanical expanding of an otherwise occluded or partially occluded blood vessel. Therefore, methods of the present invention may prevent restenosis that may otherwise occur as a result of such damage. Examples of damage that may be prevented are tearing, scratching, stretching, scraping, bruising and/or inflammation or injury caused by inflammation or other injury that may occur in a blood vessel undergoing a procedure, for example, a procedure where the inner diameter of the blood vessel is expanded using mechanical force.

Though the mechanism of operation of botulinum toxin in preventing damage from occurring in a blood vessel is not completely understood, without wishing to limit the invention to any particular theory or mechanism of operation, the inventor suggests at least two possible theories of operation.

In one instance, the toxins are thought exert a dilating effect on blood vessels thereby increasing the diameter of a vessel, including the inner diameter of the vessel. Optical coherence topography may be used to provide a measure of the dilating effect of the toxin. The dilating effect of the toxin may be quantitated as a factor of the original size of the blood vessel opening before administration of the toxin. In one embodiment, the blood vessel opening may be dilated to between about 1.5× and about 100× the size of the opening before administration of the toxin. For example, the blood vessel opening may be dilated to between about 2× and about 5× the size of the opening before administration of the toxin. In another example the blood vessel opening may be dilated to between about 2× and about 10× the size of the opening before administration of the toxin. In another example the blood vessel opening may be dilated to between about 2× and about 30× the size of the opening before administration of the toxin. In another example the blood vessel opening may be dilated to between about 2× and about 50× the size of the opening before administration of the toxin. In another example the blood vessel opening may be dilated to between about 50× and about 100× the size of the opening before administration of the toxin.

The dilating of the blood vessels may make the vessels more receptive to intervention procedures. For example, balloon angioplasty and/or insertion of a stent or other mechanical intervention may be less likely to damage the blood vessel when the blood vessel is in the dilated state. After administration of an agent to the blood vessel, the blood vessel may be allowed to dilate before the procedure, for example, an angioplasty procedure, is performed. Whether dilation has taken place, and to what extent dilation has taken place can be determined by a physician of ordinary skill. For example, optical coherence topography may be used to make these determinations.

In another non-limiting theory of operation, it is believed that the toxins disclosed herein act on inflammation mediating cells, for example, blood vessel endothelial cells. These cells present many biologically active inflammation mediators which may include bradykinin, nitric oxide and vasoactive intestinal peptide. Release of these and/or other mediators may contribute to the events which cause blood vessel inflammation which may contribute to restenosis.

During secretion or exocytosis, the mediators may be included in vesicles which fuse to the inner surface of the cell membrane thereby releasing the vesicle contents to the outside of the cell. It is theorized that interference with the exocytosis process may be the mode of action of the Clostridial toxins.

It is theorized that Clostridial toxins may operate by preventing or reducing the secretion of inflammation producing molecules in blood vessel cells or other,cells by cleaving or by otherwise interfering with the function of proteins involved in the secretory process by use of a light chain component, for example, a botulinum light chain component. A heavy chain component, for example $H_N$, may also function in certain embodiments of the present invention by, for example, assisting in the release of an agent of the invention from intracellular vesicles, for example, endosomes.

Without wishing to limit the invention to any theory or mechanism of operation, it is conjectured that inflammation may either directly; or indirectly contribute to restenosis. By preventing or reducing blood vessel inflammation that may be associated with cardiovascular procedures, for example, balloon angioplasty and/or insertion of a stent, restenosis may be reduced in a patient who has undergone a cardiovascular procedure.

Another possible mechanism for the efficacy of the present disclosed invention is an effect of a botulinum toxin to inhibit neuronally mediated blood vessel contraction. Pretreatment with a botulinum toxin can inhibit a post stretch constriction. Within the scope of the present invention is a botulinum toxin which is a targeted toxin wherein the native binding moiety of the toxin has been replaced in whole or in part by a new binding moiety which targets the toxin to alpha2 receptors on sympathetic neurons which innervate the blood vessel to be treated. Furthermore, NO can be induced locally to cause dilation.

The neurotoxin for use in accordance with the present invention may comprise a targeting component, a therapeutic component and a translocation component.

In one embodiment, the targeting component comprises a carboxyl end fragment of a heavy chain of a butyricum toxin, a tetani toxin or a botulinum toxin including botulinum toxin types A, B, C, D, E, F and G.

In another embodiment the targeting component may be of non-botulinum toxin origin. Examples of targeting components that may be used in the present invention include, but are not limited to, antibodies, monoclonal antibodies, antibody fragments (Fab, F(ab)'$_2$, Fv, ScFv, and other antibody fragments of the like), lectins, hormones, cytokines, growth factors, peptides, carbohydrates, lipids, glycons and nucleic acids. Other targeting components that may be useful in accordance with the present invention are disclosed in WO 01/21213 which is incorporated in its entirety herein by reference.

One exemplary targeting component for use in accordance with the present invention is substance P or substances similar to substance P. Use of substance P, or substances similar to substance P, as targeting components is described in U.S. patent application Ser. Nos. 09/489,667; 09/922,093 and 09/625,098 each of which is incorporated in its entirety herein by reference.

The therapeutic component operates to selectively cleave proteins essential for recognition and docking of secretory vesicles with the cytoplasmic surface of the plasma membrane, and fusion of the vesicles with the plasma membrane. One effect of the therapeutic component may be to substantially interfere with the release of neurotransmitters from a cell. Another effect of the therapeutic component may be to cause dilation of blood vessels. Another effect may be to cause flaccid paralysis of smooth muscle tissue. Another effect may be to reduce or eliminate secretion from cells, for example, inflammation producing cells. In one embodiment, the therapeutic component comprises a light chain of a butyricum toxin, a tetani toxin, a botulinum toxin, for example, botulinum toxin type A, B, C, D, E, F and G.

The translocation component may facilitate the transfer of at least a part of the neurotoxin, for example the therapeutic component into the cytoplasm of the target cell. In one embodiment, the translocation component comprises an amino end fragment of a heavy chain of a butyricum toxin, a tetani toxin, a botulinum toxin, for example, botulinum toxin type A, B, C, D, E, F and G.

According to a broad aspect of this invention, recombinant DNA methodologies may be used to produce the components of agents useful in accordance with the invention. These techniques may include steps of obtaining cloned genes from natural sources, or from synthetic oligonucleotide sequences, which may encode botulinum neurotoxin components including botulinum neurotoxin heavy chains, light chains or variants thereof, modified botulinum neurotoxin chains and/or fragments of the chains. Cloned genes may also encode a targeting component.

The genes may be cloned into, for example, cloning vectors, such as phages or plasmids or phagemids. The recombinant vectors are transformed into host cells, for example, into a prokaryotic cell, for example, *E. coli*. Proteins can be expressed and then isolated using conventional techniques.

Fusion genes may be used which encode more than one component of an agent. For example, a targeting component and a botulinum toxin heavy chain and/or light chain and/or a fragment of a heavy and/or a fragment of a light chain, can be produced from a single cloned gene as a fusion protein. Alternatively, individual components obtained from recombinant techniques can be chemically coupled to other components obtain from similar or other sources. For example, a targeting component may be coupled to a recombinant L chain or to a recombinant fusion $LH_N$. The linkages between the botulinum components and the targeting moieties may include appropriate spacer components, which may also be DNA encoded.

In one embodiment, an $LH_N$, which may be a hybrid of an L chain and an $H_N$ from different botulinum toxin types, is expressed recombinantly as a fusion protein. Such an $LH_N$ hybrid may also be coupled to a targeting component. There may be included one or more spacers between the L and $H_N$ and/or between the $LH_N$ and targeting component.

In another embodiment of the invention, the L chain of a botulinum neurotoxin, or a fragment of the L chain containing the endopeptidase activity, is expressed recombinantly to produce an agent for use in accordance with the present invention.

In another embodiment of the invention, the L chain of a botulinum neurotoxin, or a fragment of the L chain containing the endopeptidase activity, is expressed recombinantly as a fusion protein with the $H_N$ of the H chain and the targeting component. The expressed fusion protein may also include one or more spacer regions. For example, the L chain may be fused to $H_N$ which is in turn fused to the targeting component. In another example, the $H_N$ may be fused to the L chain which is in turn fused to the targeting component. Spacer components may be expressed recombinantly between some or all of the components of an agent of the invention.

In one example of producing a hybrid of $LH_N$, the L chain is obtained from botulinum toxin type B and the amine end segment of the $H_N$ chain fragment is obtained from botulinum toxin type A. The $H_N$ fragment of the botulinum toxin type A is produced according to the method described by Shone C. C., Hambleton, P., and Melling, J. (1987, Eur. J. Biochem. 167, 175–180) and the L chain of botulinum toxin type B according to the method of Sathyamoorthy, V. and DasGupta, B. R. (1985, J. Biol. Chem. 260, 10461–10466). The free cysteine on the amine end segment of the H chain fragment of botulinum toxin type A is then derivatized by the addition of a ten-fold molar excess of dipyridyl disulphide followed by incubation at 4° C. overnight. The excess dipyridyl disulphide and the thiopyridone by product are then removed by desalting the protein over a PD10 column (Pharmacia) into PBS.

The derivatized $H_N$ is then concentrated to a protein concentration in excess of 1 mg/ml before being mixed with an equimolar portion of L chain from botulinum toxin type B (>1 mg/ml in PBS). After overnight incubation at room temperature the mixture is separated by size exclusion chromatography over Superose 6 (Pharmacia), and the fractions analyzed by SDS-PAGE. The chimeric $LH_N$ is then available to produce a conjugated agent which includes a targeting component.

The example described above is purely illustrative of the invention. In synthesizing the agents, the coupling of the targeting, moieties to the botulinum components, for example the modified botulinum neurotoxins or fragments thereof, may be achieved via chemical coupling using reagents and techniques known to those skilled in the art. Thus, any coupling chemistry capable of covalently attaching the targeting moieties of the agents to botulinum neurotoxin components and known to those skilled in the art is covered by the scope of this application.

Modified botulinum toxins which have an altered biological persistence and/or biological activity are contemplated for use in the present invention. U.S. patent applications Ser. Nos. 09/620,840 and 09/910,346 include examples of compositions and methods for altering the biological persistence of botulinum toxins. These two patent applications are incorporated in their entirety herein by reference.

A biological persistence enhancing component and/or a biological activity enhancing component, for example, a leucine based motif, may be added to a botulinum neurotoxin thereby increasing the biological persistence and/or biological activity of the botulinum neurotoxin. Similarly, a biological persistence enhancing component can be removed from a botulinum neurotoxin thereby decreasing the biological persistence and/or biological activity of the neurotoxin.

The botulinum neurotoxin can be a hybrid neurotoxin. For example, the neurotoxin's targeting, translocation and therapeutic components may be derived from different botulinum toxin serotypes. For example, the polypeptide may comprise a first amino acid sequence region derived from the $H_C$ of a botulinum toxin type A, a second amino acid sequence region derived from the $H_N$ Of botulinum type B, and a third amino acid sequence region derived from the light chain of botulinum serotype E. This is merely an example and all other possible combinations are included within the scope of the present invention.

The neurotoxin's targeting, translocation and therapeutic components can be modified from the naturally occurring sequence from which they are derived. For example, the amino acid sequence region can have at least one or more amino acids added, deleted or substituted as compared to the naturally occurring sequence.

Amino acids that can be substituted for amino acids contained in a biological persistence enhancing component include alanine, aspargine, cysteine, aspartic acid, glutamic acid, phenylalanine, glycine, histidine, isoleucine, lysine, leucine, methionine, proline, glutamine, arginine, serine, threonine, valine, tryptophan, tyrosine and other naturally occurring amino acids as well as non-standard amino acids.

Methods of the present invention provide for reduction in restenosis ranging from about 1% to about 100% in effectiveness. For example, the reduction may be between about 1% and about 10% or between about 10% and about 20% or between about 10% and about 30% or between about 10% and about 40% or between about 10% and about 50% or between about 10% and about 60% or between about 10% and about 70% or between about 10% and about 80% or between about 10% and about 90% or between about 10% and about 100%.

Generally, the dose of neurotoxin to be administered may vary with the age, presenting condition and weight of the patient to be treated. The potency of the neurotoxin will also be considered. Toxin potency is expressed as a multiple of the $LD_{50}$ value for a mouse. One "unit" of toxin can be defined as the amount of toxin that kills 50% of a group of mice that were disease-free prior to inoculation with the toxin. For example, commercially available Botulinum toxin A typically has a potency such that one nanogram contains about 40 mouse units. The potency, or $LD_{50}$ in humans of the Botulinum toxin A product supplied by Allergan, Inc. under the registered trademark "BOTOX" is believed to be about 2,730 mouse units.

The neurotoxin can be administered in a dose of about 0.001 units up to about 100 units. In one embodiment, individual dosages of about 0.01 units to about 5 units are used. In another embodiment, individual dosages of about 0.01 units to about 3 units are used. In still another embodiment, individual dosages of about 0.01 units to about 1 unit are used. In still another embodiment, individual dosages of about 0.05 units to about 1 unit are used. Those of ordinary skill in the art will know, or can readily ascertain, how to adjust dosages for neurotoxin of greater or lesser potency in a certain circumstance.

For modified or variant botulinum toxins potency may be expressed as a multiple of the $LD_{50}$ value of an agent of the invention for a mouse. A "U" or "unit" of an agent can be defined as the amount of toxin that kills 50% of a group of mice that were disease-free prior to inoculation with the agent. Alternatively, potency may be expressed as the $LD_{50}$ value of an agent that would be produced by an equal molar amount of a native, non-variant botulinum toxin.

Preferably, the lowest therapeutically effective dosage will be administered to the patient. The lowest therapeutic dosage is that dosage which results in the desired effect on a blood vessel of the patient to which the toxin is administered. Methods for assessing or quantifying the effect of a toxin on a blood vessel can be determined by those skilled in the art. For example, use of optical coherence topography can provide a measure of the dilating effect of the toxin.

In an initial treatment, a low dosage may be administered to determine the patient's sensitivity to, and tolerance of, the neurotoxin. Additional administrations of the same or different dosages may be administered to the blood vessel as necessary. For example, a toxin may be administered to a blood vessel before a procedure, for example, a coronary angioplasty procedure, is performed, and/or during the procedure and/or after the procedure. The number of administrations and timing of the administrations may be determined by the treating physician.

The neurotoxins may be administered by, for example, injection into a blood vessel using a needle or by needleless injection. The toxin may also be administered by application of the toxin to the wall of the blood vessel in a salve, lotion, ointment, cream, emulsion or the like delivery substrates.

In one embodiment, an agent of the invention is administered to the patient by injection. For example, an agent may be injected into the cardiovascular system of a patient. In particular, the injecting may be into an artery, for example, a coronary artery. Typically, the injecting is into the region of the blood vessel where the vessel is to undergo a procedure, for example, a procedure to mechanically expand the internal diameter of an occluded blood vessel.

An agent may be injected into the wall of a blood vessel from outside of the blood vessel or an agent may be injected into the wall of a blood vessel from inside the blood vessel. Methods for injecting into a wall of a blood vessel are well known to those of ordinary skill in the art. For example, an agent may be injected into the wall of a blood vessel from inside the blood vessel by the use of a catheter containing one or more needles for injecting.

In needleless injection delivery methods, microprojectile drug particles may be coated with a neurotoxin and then discharged into the blood vessel from an external delivery device. Depending on the discharge velocity and the distance from the injection site, the drug particles penetrate through the different layers of the blood vessels. As the microprojectiles penetrate through, or are deposited in, the blood vessel cells, the neurotoxin is released. Individual layers of blood vessels may be targeted for the microprojectiles.

The neurotoxins may also be administered using a stent or an angioplasty balloon that is coated or impregnated with the toxin, for example botulinum toxin. U.S. Pat. Nos. 6,306,423 and 6,312,708 disclose material that may be impregnated, attached or imbedded with the toxin and which may be used to coat stents and/or angioplasty balloons. In addition, the material may be used to form stents which include the toxin. The disclosure of each of these two patents is incorporated in its entirety herein by reference. In one embodiment, the blood vessel to be treated is first administered with botulinum toxin before inserting the toxin comprising stent and/or balloon. In another embodiment, the blood vessel to be treated is not administered with toxin before inserting the botulinum toxin comprising stent and/or balloon.

Administrations may be repeated if necessary. As a general guideline, botulinum toxin A administered into a blood vessel may produce a dilating and/or anti-inflammatory effect for, for example about 1 month to about 3 months, or for example, about 3 to about 6 months or for example from about 6 months to about 1 year.

The agent may be allowed to induce its effect on a blood vessel before a procedure, for example, a coronary angioplasty procedure, is performed. For example, the agent may be allowed to dilate the blood vessel and/or prevent inflammation of the blood vessel before a procedure is begun. A physician of ordinary skill can determine when the agent has exerted its effect(s) on a blood vessel.

The invention having been fully described, examples illustrating its practice are set forth below. These examples should not, however, be considered to limit the scope of the invention, which is defined by the appended claims.

EXAMPLES

Example 1

Use of Botulinum Toxin in Balloon Angioplasty where a Stent is Not Used

A 54 year old male patient complains of chest pains in an emergency room examination. The patient smokes 2 to 3 packs of cigarettes a day, is of average weight and has a family history of coronary arterial blockage. The patient is diagnosed as having an occlusion of the left coronary artery. A coronary angiogram is used to measure the narrowing of the arteries. It is estimated that the patient suffers from an 80% occlusion of the left coronary artery. He is scheduled for a balloon angioplasty procedure for the following week.

The physician begins the procedure by injecting between about 0.05 units and about 5 units of botulinum toxin type A into the wall of the left coronary artery of the patient. Following injection, the artery is allowed to dilate. A 3-millimeter noncompliant balloon catheter is then inserted into the femoral artery of the patient through the groin/upper thigh area. The catheter is then fed through the artery up into the heart using a video monitor to guide the process. A guide wire is advanced to the location of the blocked artery, and the balloon catheter is passed along the guide wire into the target area of coronary blockage. When the catheter reaches the target area, the balloon is inflated for a period of several seconds to several minutes. After deflation of the balloon, the same area may be treated with one or more additional inflations. Examination reveals little or no damage to the treated artery.

One year after the procedure there is no sign of restenosis and the patient appears in good health.

Example 2

Use of Botulinum Toxin in Balloon Angioplasty where a Stent is Used

A 62 year old male patient who is approximately 30% overweight and has a serum cholesterol level of approximately 260 complains of chest pains. The patient is diagnosed as having coronary artery blockage and is scheduled for a percutaneous transluminal coronary angioplasty procedure.

Between about 0.01 units to about 1 unit of botulinum toxin is injected directly into the wall of the artery in the area of the blockage. Following injection, the artery is allowed to dilate. A 3-millimeter compliant balloon catheter and stent are then inserted into the interosseous artery of the patient through the wrist area. The catheter and stent are then fed through the interosseous artery to the area of blockage. A guide wire is advanced to the location of the blocked artery, and the catheter and stent are passed along the guide wire into the target area of coronary blockage. When the catheter reaches the target area, the balloon is inflated and the stent is correspondingly expanded bracing open the artery. The balloon is deflated and removed leaving in place the expanded stent. There is no sign of damage to the artery.

Six months after the procedure there is no sign of restenosis and the patient appears in good health.

Example 3

Use of Botulinum Toxin in Balloon Angioplasty with a Stent to Treat an Advanced Case of Restenosis A 49 year old male patient is diagnosed with coronary arterial blockage as a result of restenosis. The patient has a history of coronary arterial blockage and has previously undergone a balloon angioplasty procedure. Six months after the procedure, the patient is diagnosed with an advanced case of restenosis.

The patient undergoes a percutaneous transluminal coronary angioplasty procedure in which botulinum toxin type A, B, C, D, F and/or G is used. Between about 0.1 units and about 4 units of botulinum toxin is injected into the wall of the blood vessel in the area of restenosis. Following injection, the artery is allowed to dilate. A 4-millimeter compliant balloon catheter and stent are then inserted into the femoral artery of the patient. The catheter and stent are then fed through the artery to the area of blockage using a video monitor to guide the process. A guide wire is advanced to the location of the blocked artery, and the catheter and stent are passed along the guide wire into the target area of coronary blockage. When the catheter and stent reach the target area, the balloon is inflated and the stent correspondingly expanded holding open the artery. The balloon is deflated and removed leaving in place the expanded stent. 3 to 6 months after the procedure, the blood vessel is re-injected with the botulinum toxin in the area of the stent.

Two years after the procedure there is no sign of restenosis and the patient appears in good health.

Example 4

Balloon Angioplasty where a Stent Impregnated with Botulinum Toxin is Used

A 58 year old female patient is diagnosed with coronary arterial blockage. The patient is scheduled for a percutaneous transluminal coronary angioplasty procedure in which a stent impregnated with botulinum toxin type A, B, C, D, E, F and/or G is used.

Between about 0.1 units and about 2 units of a botulinum toxin is injected into the wall of the blood vessel in the area of blockage. Following injection, the artery is allowed to dilate. A 2-millimeter compliant balloon catheter and stent, which is coated or impregnated with a botulinum toxin, are then inserted into the femoral artery of the patient. The catheter and stent are passed through the femoral artery to the area of blockage using a video monitor to guide the process. A guide wire is advanced to the location of the blocked artery, and the catheter and stent are passed along the guide wire into the target area of coronary blockage. When the catheter and stent reach the target area, the balloon is inflated and the stent is correspondingly expanded bracing open the artery. The balloon is deflated and removed leaving in place the expanded stent.

One year after the procedure there is no sign of restenosis and the patient appears in good health.

Example 5

Balloon Angioplasty where a Self Expanding Stent Impregnated with Botulinum Toxin is Used A 50 year old male patient is diagnosed with coronary arterial blockage of the left coronary artery and is scheduled for a percutaneous transluminal coronary angioplasty procedure in which a self expanding stent impregnated with a botulinum toxin is used.

The physician begins the procedure by injecting between about 0.1 units and about 5 units of botulinum toxin type A into the wall of the left coronary artery of the patient. Following injection, the artery is allowed to dilate. A self expanding stent impregnated with the botulinum toxin is then inserted with a catheter into the common interosseous artery of the patient through the wrist area. The catheter and stent are passed through the interosseous artery to the area of blockage. A guide wire is advanced to the location of the blocked artery advancing the botulinum toxin impregnated, self expanding stent into the target area of coronary blockage. When the catheter reaches the target area, the stent is expanded bracing open the artery.

Two years after the procedure there is no sign of restenosis and the patient appears in good health.

Example 6

Injection of Botulinum Toxin by Use of a Catheter Injecting System

A 51 year old female patient complains of chest pains. The patient is overweight and has a serum cholesterol level of approximately 270. The patient is diagnosed as having coronary artery blockage. A coronary angiogram is used to measure the narrowing of the arteries. It is estimated that the patient suffers from a 70% to 90% occlusion of a coronary artery. She is scheduled for a percutaneous transluminal coronary angioplasty procedure.

Between bout 0.01 units and about 3 units of a botulinum toxin is injected directly into the wall of the artery in the area of the blockage. For injection, a catheter which includes one or more injection needles is inserted through the femoral artery of the patient through the groin/upper thigh area into the area of the coronary blockage. There the botulinum toxin is injected into the inner wall of the occluded blood vessel.

Following injection of the botulinum toxin, the artery is allowed to dilate. A 3-millimeter compliant balloon catheter and stent impregnated with botulinum toxin type A are then inserted into the femoral artery of the patient. The catheter and stent are fed through the femoral artery to the area of blockage using a video monitor to guide the process. A guide wire is advanced to the location of the blocked artery, and the catheter and stent is passed along the guide wire into the target area of coronary blockage. When the catheter reaches the target area, the balloon is inflated and the stent is correspondingly expanded bracing open the artery. The balloon is deflated and removed leaving in place the expanded stent. There is no sign of damage to the blood vessel.

One year after the procedure there is no sign of restenosis and the patient appears in good health.

My invention also includes within its scope the use of a neurotoxin, such as a botulinum toxin, in the preparation of a medicament for the treatment of a cardiovascular disease.

All references, articles, patents, applications and publications set forth above are incorporated herein by reference in their entireties.

Accordingly, the spirit and scope of the following claims should not be limited to the descriptions of the preferred embodiments set forth above.

We claim:

1. A composition for use in a cardiovascular procedure comprising a stent with a therapeutically affective amount of a botulinum neurotoxin attached or embedded therein wherein the botulinum neurotoxin elutes from the stent.

2. The composition of claim 1 wherein the botulinum neurotoxin is botulinum neurotoxin type A.

3. The composition of claim 1 wherein the botulinum neurotoxin is selected from the group consisting of botulinum neurotoxins A, B, C, D, E, F and G.

4. A self-expanding stent for use in a cardiovascular procedure comprising a therapeutically effective amount of a botulinum neurotoxin attached or embedded therein.

5. An angioplasty balloon for use in a cardiovascular procedure comprising a therapeutically effective amount of a botulinum neurotoxin attached or embedded therein.

* * * * *